United States Patent [19]

Story et al.

[11] 3,960,897

[45] June 1, 1976

[54] METHOD FOR THE PREPARATION OF MACROCYCLIC COMPOUND

[75] Inventors: Paul Richard Story, Athens, Ga.; Peter Busch, Willich, Germany; Donald Derby Denson, Kettering, Ohio; Carl Edward Wright, Athens, Ga.

[73] Assignee: Research Corporation, New York, N.Y.

[22] Filed: Mar. 29, 1974

[21] Appl. No.: 456,315

Related U.S. Application Data

[63] Continuation of Ser. No. 238,936, March 28, 1972, abandoned, which is a continuation-in-part of Ser. No. 842,739, July 17, 1969, abandoned, which is a continuation-in-part of Ser. No. 697,593, Jan. 15, 1968, Pat. No. 3,528,898.

[52] U.S. Cl. .................... 260/343; 204/158 R; 204/158 HA; 252/522; 260/340.2; 260/535 R; 260/537 R

[51] Int. Cl.$^2$ .................... C07D 313/00
[58] Field of Search .................... 260/343

[56] References Cited

UNITED STATES PATENTS

| | | | |
|---|---|---|---|
| 2,163,268 | 6/1939 | Carothers et al. | 260/343 |
| 3,528,898 | 9/1970 | Story | 204/158 |
| 3,784,567 | 1/1974 | Isard et al. | 260/343 |

OTHER PUBLICATIONS

Story et al., J. Amer. Chem. Soc., vol. 90, No. 3, (1/31/68), pp. 817, 818.

*Primary Examiner*—James A. Patten
*Attorney, Agent, or Firm*—Dennis P. Clarke

[57] ABSTRACT

A method for the preparation of macrocyclic compounds comprising heating a mixture of a cyclic peroxide and an alkane solvent.

9 Claims, No Drawings

METHOD FOR THE PREPARATION OF MACROCYCLIC COMPOUND

This is a Continuation, of application Ser. No. 238,936, filed Mar. 28, 1972, now abandoned, which is a continuation-in-part application of application Ser. No. 842,739, filed July 17, 1969, now abandoned, which, in turn, is a continuation-in-part application of application Ser. No. 697,593, filed Jan. 15, 1968, now U.S. Pat. No. 3,528,898.

BACKGROUND OF THE INVENTION

The production of macrocyclic hydrocarbons and lactones by the thermal decomposition or photolyzation of di and tri-meric cyclic peroxides is known. The thermal decomposition of peroxides is disadvantageous, however, in that the thermal reaction is difficult to control and susceptible to explosions. The photolytic process must also be cautiously carried out at high dilutions. These prior art processes require the use of expensive and bulky equipment and/or large quantities of diluent liquids thereby rendering them less amenable to large batch or continuous flow methods.

The above-described prior art processes are more particularly described in U.S. Pat. No. 3,528,898 (to Paul R. Story) and Story et al, J.A.C.S., Vol. 90, pp. 817–18 (January 31, 1968). The thermolytic process is not only susceptible to explosions but is also productive of mixtures of macrocyclic hydrocarbons and lactones wherein the proportions of lactones are relatively small. The photolytic process is productive of relatively low yields of both the macrocyclic hydrocarbons and lactones.

SUMMARY OF THE INVENTION

The invention involves a process for producing a mixture of macrocyclic hydrocarbons and lactones in high yields wherein the ratios of lactone to hydrocarbon are relatively high by heating a mixture of a di- or tri-meric cyclic peroxide and an alkane solvent.

DETAILED DESCRIPTION OF THE INVENTION

The di- and tri-meric cyclic peroxides (more properly termed dicycloalkylidene and tricycloalkylidene peroxides, respectively) which are employed as starting materials in the process of the invention may be represented by the following structural formulae:

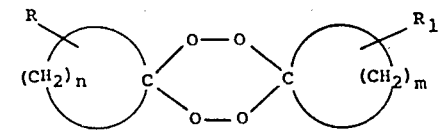

dimeric peroxide and,

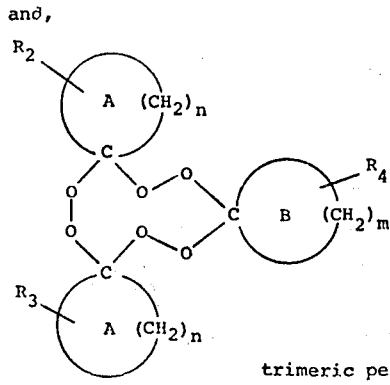

trimeric peroxide wherein n is a positive integer above 3, preferably 4 to 17; and R, $R_1$, $R_2$, $R_3$ and $R_4$ may be the same or different and are selected from the groups consisting of hydrogen, hydroxy, halogen, alkoxy, acyloxy (preferably lower alkanoyloxy), carboxyl, hydroxyalkyl, haloalkyl, alkoxy alkyl, acyloxy (preferably lower alkanoyloxy) alkyl, carboxyl alkyl, aryl, hydroxy aryl, halo aryl, alkoxy aryl, acyloxy (preferably lower alkanoyloxy) aryl, carboxyl aryl, amido, amino, amino alkyl and amino aryl, wherein said alkyl and substituted alkyl groups are lower alkyl groups and said aryl groups are preferably monocyclic aryl groups. Moreover, one or more of the methylene groups in the cyclic peroxides may be substituted by a heteroatom such as oxygen, nitrogen and sulfur. The peroxides are conventionally termed di- and tri-cycloalkylidene peroxides.

The di-meric peroxides may be prepared by any of a variety of known methods, i.e., those described by R. Criegee et al, Ann., 583, 6 (1953); M. S. Kharasch et al, J. Org. Chem., 23, 1322 (1958), and T. Ledaal, ACTA Chem. Scand., 21, 1656 (1967). The tri-meric peroxides may be prepared by any of the methods described by R. Criegee et al, Ann., 565, 7 (1949) and W. Dilthey et al, J. prakt. Che., 154, 219 (1940).

A unique and novel method for producing mixtures of the di- and tri-meric cyclic peroxides is described in copending application Ser. No. 842,689 (filed July 17, 1969 by Story et al).

The di-meric cyclic peroxides decompose when heated in admixture with an alkane solvent to yield a mixture of macrocyclic compounds of the general formulae:

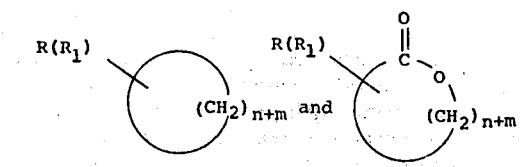

wherein n, m, R and $R_1$ have the values noted above.

The tri-meric cyclic peroxides decompose when heated in admixture with an alkane solvent to yield a mixture of macrocyclic compounds of the general formulae:

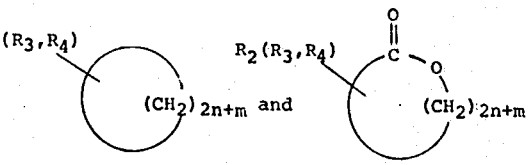

As noted hereinabove, the thermolytic decomposition of these peroxides to the corresponding macrocyclic compounds is known. It is further suggested in the prior art to carry out these decomposition processes in the presence of small amounts of solvents such as methanol and benzene to avoid explosions. The present invention is predicated on the discovery that the inclusion of relatively large amounts of alkane solvent in the thermolytic decomposition media not only avoids explosions but also results in increased yields of the macrocyclic compounds and an increase in the proportion of the lactone component of the mixture.

The alkanes which may be employed in the process of the invention include those capable of dissolving the starting peroxide, i.e., decane, nonane, dodecane, undecane, etc.

The amount of alkane solvent employed in the thermolytic decomposition process is at least about 1 part by weight of solvent per part of peroxide starting material. The only limitations as to the maximum amount of solvent which may be employed is the expense of and availability of the solvent. Amounts as high as 100,000 parts by weight of solvent per part of peroxide may be utilized. It is preferred to employ from about 4 to about 8 parts by weight of alkane solvent per part of peroxide.

The admixture of peroxide and alkane solvent is heated to a temperature of from about 100°C. to about 350°C., preferably about 180°C., to achieve thermolytic decomposition. The reaction time may vary from a few minutes up to several days, preferably from about 30 minutes to about 180 minutes.

The macrocyclic compounds produced according to the process of the invention are valuable musk-type compounds useful in the perfume or odorant industry. The macrocyclic lactones are particularly useful in perfumes as indicated by P. Z. Bedoukian, Amer. Perf. Cosmet. 80, 23 (1965) and in Perfumery Synthetics and Isolates, D. Van Nostrand, N.Y., (1951). The process of the invention affords a new route to these lactones in increased yields. The macrocyclic hydrocarbons produced in admixture with the lactones are valuable in the perfume industry. For example, cyclopentadecane may be oxidized by the well-known photooximination method employing nitrosyl chloride and the resulting oxime hydrochloride readily hydrolyzed to cyclopentadecanone which is a highly valued odorant with a pure musk odor. Alternatively, the cyclopentadecane may be halogenated in the presence of light, the resultant cyclopentadecanyl halide hydrolyzed with weak alkali to the alcohol and the alcohol oxidized with dichromate to cyclopentadecanone. Where the starting peroxide reactant contains a carbonyl group, the ketone may be produced directly.

Where the products contain two or more functional substituents they may be employed to prepare elastomeric polyesters and polyamides.

The invention is illustrated by the following nonlimiting examples.

EXAMPLE I

A solution of 180 ml. of decane and 40 grams of dicyclohexylidenecyclopentylidene peroxide was refluxed at 180°C. for 3 hours at which time the heat was removed and the reaction solution left standing at room temperature overnight. A small amount of a deposit of a residue of a heavy oil was found in the reaction solution. The solution was decanted and the decane distilled off using a short path column. Distillation of the product using a spinning band column yielded 4.22 grams of cyclotetradecane, b.p. 77°–78°C. at 0.4 mm., 17.2 percent yield, and 6.17 grams of cyclopentadecanolide, b.p 114°C. at 0.5 mm., 22.2 percent yield. Both products were identified by infrared, nuclear magnetic resonance and, mass spectrometric analysis. The lactone cyclopentadecanolide is known in the perfume chemicals business as Exaltolide, a trademark of Firmenich et Cie and as Thibetolide, a trademark of Givaudan, Inc.

EXAMPLE II

A solution of 10 ml. decane and 700 mg. of dicyclohexlidenecycloheptylidene peroxide was refluxed for 2.1 hours at 180°C. The product mixture was analyzed and the products isolated by preparative gas chromatography using a Varian-Aerograph Model 1200 HY-FY III gas chromatograph fitted with an effluent splitter and a 5 ft. by ¼ in. column packed with Chromosorb W (Johns-Manville) coated with 20 percent by weight Dow SE-30 silicone gum rubber. Nitrogen carrier gas was used. Product yields were determined by calibration of detector response using known solutions of authentic materials according to standard techniques. Analysis of the product solution by gas chromatographic technique revealed the cyclohexadecane was obtained in a 25 percent yield. The lactone cycloheptadecanolide was obtained in a 20 percent yield. Identity of the products was established by infrared nuclear magnetic resonance, and mass spectrometric analysis of the isolated product.

EXAMPLE III

The following Table I illustrates the pyrolysis of a number of peroxides with various amounts of peroxides, various amounts of solvent, decane, and various refluxing time periods.

TABLE I

| Peroxide | m.p. C° | Weight | Decane | Reflux Time | Hydrocarbon | Yield % | Lactone | Yield % |
|---|---|---|---|---|---|---|---|---|
| Tricyclopentylidene [n=m=4] | 170° | 600 mg | 10 ml | 2.67 hr | Cyclododecane | 30 | Cyclotridecanolide | 20 |
| Dicyclopentylidene-cyclohexylidene [n=4, m=5] | 51–81° | 670 mg | 10 ml | 1.67 hr | Cyclotridecane | 20 | Cyclotetradecanolide | 15 |
| Dicyclopentylidene-cycloheptylidene [n=4, m=6] | 81–86° | 500 mg | 10 ml | 2.0 hr | Cyclotetradecane | 20 | Cyclopentadecanolide | 15 |
| Dicyclohexylidene-3-methylcyclohexylidene [n=m=5]3-methyl in ring B] | oil | 100 mg | 2ml | 4.25 hr | Methylcyclopentadecane | 15 | Methylcyclohexadecanolide (apparently mixture of isomers) | 25 |
| Dicyclohexylidene-4-methylcyclohexylidene [n=m=5, 4-methyl in ring B] | oil | 420 mg | 10 ml | 1.0 hr | Methylcyclopentadecane | 15 | Methylcyclohexadecanolide (probably mixture of isomers) | 25 |
| Dicycloheptylidene-cyclopentylidene | 92–95° | 50 mg | 1.5 | 3.0 | Cyclohexadecane | 5 | Cycloheptadecanolide | 5 |

TABLE I-continued

| Peroxide | m.p. C° | Weight | Decane | Reflux Time | Hydrocarbon | Yield % | Lactone | Yield % |
|---|---|---|---|---|---|---|---|---|
| [n=6, m=4] Dicycloheptylidene-cyclohexylidene | oil | 500 mg | 10 ml | 2.0 hr | Cycloheptadecane | 3 | Cyclooctadecanolide | 3 |
| [n=6, m=5] Tricycloheptylidene | 78–80° | 500 mg | 10 ml | 2.0 hr | Cyclooctadecane | 15 | Cyclononadecanolide | 15 |
| [n=m=6] Dicycloheptylidene-cycloododecylidene | oil | 500 mg | 10 ml | 2.0 hr | Cyclotricosane | 25 | Cyclotetracosanolide | 20 |
| [n=6, m=11] Tricyclooctylidene | 72–75° | 400 mg | 10 ml | 3.0 hr | Cycloheneicosane | 5 | Cyclodocosanolide | 10 |
| [n=m=7] Di(4,methylcyclohexylidene) cyclohexylidene [n=m=5, 4-methyl group in each A ring] | | 550 mg | 11 ml | 2.0 hr | 1,6-Dimethyl-cyclopentadecane | 20 | Dimethylcyclohexa-decanolide (probably mixture of isomers) | 20 |

EXAMPLE IV

Using the same procedure as in Example I, 580 mg. of dicycloheptylidene peroxide was pyrolyzed using 10 ml. of decane for 1.33 hours.

Gas chromatographic analysis gave the hydrocarbon cyclododecane in 15 percent yield, and the lactone cyclotridecanolide in 25 percent yield. This yield of the lactone is a vast increase over the prior art thermal methods.

EXAMPLE V

A solution of 50 grams of tricyclohexylidene peroxide in 785 ml. of undecane was heated at reflux temperature of 194°C. for three hours. After cooling, the reaction mixture was washed three times each with saturated sodium carbonate solution and water and then dried over anhydrous sodium sulfate.

Vacuum distillation of the mixture using an annular Teflon still gave 5 grams of cyclopentadecane, b.p. 84° 0.15 mm., a yield of 16.3 percent, and 7.12 grams of the lactone cyclohexadecanolide (dihydroambrettolide), b.p. 120° 0.15 mm., a yield of 19.4 percent. Structure of the products was confirmed as in Example II.

EXAMPLE VI

The following Table II illustrates the pyrolysis of tricyclohexylidene peroxide with varying conditions as to solvent, temperature, reaction time and amounts of peroxide used.

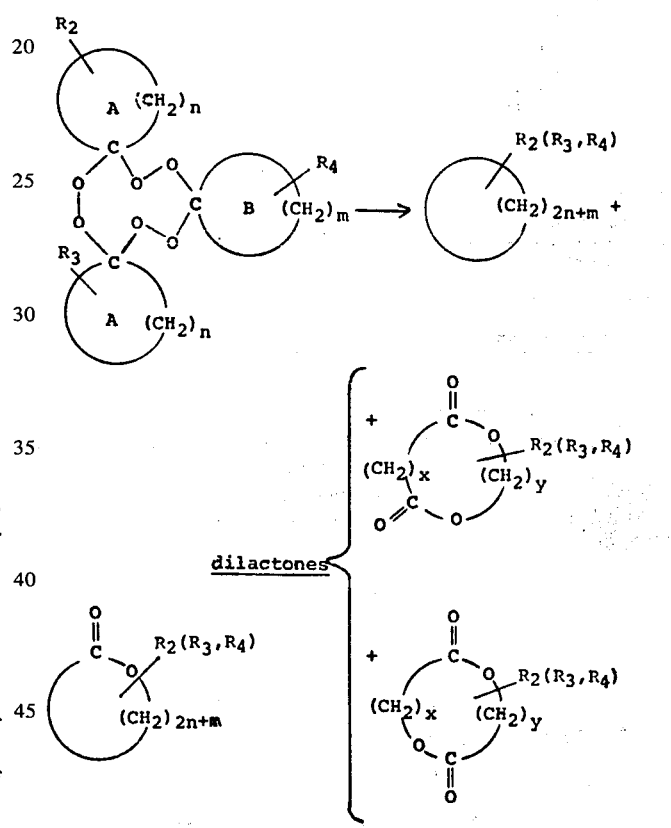

TABLE II

| Solvent | Volume ml | Peroxide mg | Temp. C° | Reaction Time | Cyclopentadecane percent yield | Cyclohexadecanolide percent yield |
|---|---|---|---|---|---|---|
| dodecane | 11 | 700 | 209° | 1 hr. | 17.5 | 14.5 |
| decane | 11 | 700 | 174° | 3 hr. | 19.2 | 22.0 |
| nonane | 11 | 700 | 156° | 24 hr. | 20.0 | 17.0 |
| Isopar K | 11 | 700 | 180° | 15 min. | 25.0 | 26.0 |

Isopar K is a Humble Oil Co. tradename for their saturated hydrocarbon solvent with the boiling range 176°–197°C.

Not only does the process of the present invention produce macrocyclic compounds such as the lactone and the original hydrocarbon compound, but it has been discovered that the same reaction produces dilactones from tricycloalkylidene peroxides. These dilactones do not result from the decomposition of dicycloalkylidene peroxides. These tricycloalkylidene peroxides decompose according to the following general formula:

Where:
1. if $x = n+m$, then $y = n$
2. if $x = 2n$, then $y = m$ wherein $R_2$, $R_3$ and $R_4$ have the meanings set forth above.

These macrocyclic dilactones are obtained as mixtures of isomers as shown in the above general reaction. They are useful as musk compounds, and when hydrolyzed they will afford difunctional alcohol-acids useful as monomers in the production of polyesters.

EXAMPLE VII

The examples listed in the following Table IV are those same reactions listed in Table I and are so identified. In Table III yields from decomposition of tricycloalkylidene peroxides are given.

wherein n is a positive integer in the range of from 4 to 17 inclusive; m is a positive integer in the range of from 4 to 17 inclusive; and R, $R_1$ and $R_2$ may be the same or different and are hydrogen or methyl; and (2) an alkane which is a solvent for said peroxide at a temperature of from about 100°C to about 350°C for a time sufficient to decompose said peroxide to said macrocyclic compounds; the weight ratio of said alkane to said peroxide being at least about 1:1.

TABLE III

| Peroxide | No. of carbons in Dilactone ring | Yield of Dilactone, % | Characteristic Infrared bands, (cm$^{-1}$, CCl$_4$) | Mass Spect. parent ion m/e |
|---|---|---|---|---|
| Dicyclohexylidene-cyclopentylidene [n=5, m=4] | 16 b.p.=125–130°C | 5% | 1740(s); 1170(m); 1255(m) | 284 |
| Dicyclohexylidene-cycloheptylidene [n=5, m=6] | 18 | 15% | 1745(s); 1230–1255(m) | 312 |
| Tricyclopentylidene [n=m=4] | 14 | 8–10% | 1744(s);1240–1260(w) | 256 |
| Dicyclohexylidene-cyclohexylidene [n=4, m=5] | 15 | 12% | 1740(s);1230–1255(m) | 270 |
| Dicyclohexylidene-3-methylcyclohexylidene [n=m=5, 3-methyl in ring B] | 17 | 5% | 1745(s);1180(broad,w) | 312 |
| Dicyclopentylidene-cycloheptylidene [n=4, m=6] | 16 | 8% | 1740(s);1250(broad,m) | 284 |
| Dicyclohexylidene-4-methylcyclohexylidene [n=m=5, 4 methyl in Ring B] | 17 | 15% | 1745(s); 1180(broad,w) | 312 |
| Tricycloheptylidene [n=m=6] | 20 | 7% | 1740(s); 1225(broad,w) | 340 |
| Tricyclohexylidene | 17 | 10% | 1745(s);1175(m);1240(m) | 298 |

What is claimed is:

1. A method for the preparation of a product consisting essentially of a mixture of a macrocyclic hydrocarbon and a macrocyclic lactone consisting essentially of heating a mixture of (1) a peroxide having the structural formula:

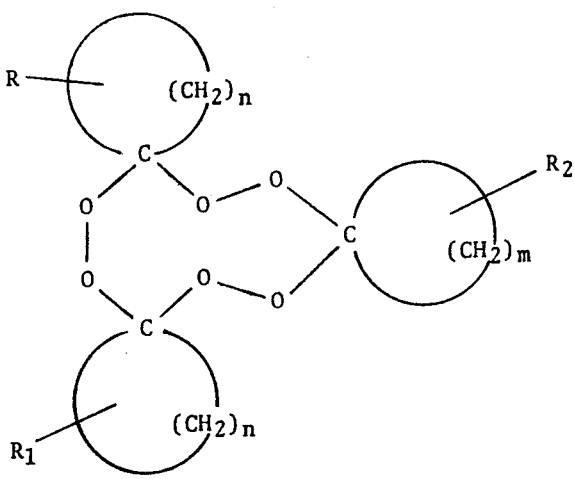

2. The method of claim 1 including the step of separating said macrocyclic hydrocarbon from said product mixture.

3. The method of claim 1 including the step of separating said macrocyclic lactone from said product mixture.

4. The method of claim 1 wherein said alkane is selected from the group consisting of nonane, decane, undecane, dodecane and mixtures thereof.

5. The method of claim 1 wherein the weight ratio of said alkane to said peroxide is in the range of from about 4:1 to about 8:1.

6. The method of claim 1 wherein the heating is carried out for a time in the range of from a few minutes to several days.

7. The method of claim 6 wherein said heating is carried out for a time in the range of from about 30 minutes to about 180 minutes.

8. The method of claim 1 wherein the temperature is about 180°C.

9. The method of preparing cyclopentadecanolide comprising dissolving 1 part of dicyclohexylidene cyclopentylidene peroxide in 4 parts of decane, heating the solution for 3 hours at 180°C and separating cyclopentadecanolide from the reaction mixture.

* * * * *